United States Patent
Pettit et al.

(10) Patent No.: US 6,569,834 B1
(45) Date of Patent: May 27, 2003

(54) ELUCIDATION AND SYNTHESIS OF ANTINEOPLASTIC TETRAPEPTIDE W-AMINOALKYL-AMIDES

(76) Inventors: George R. Pettit, 6232 Bret Hills Dr., Paradise Valley, AZ (US) 85253; Jozsef Barkoczy, Szirom utca 4-6/B, Budapest (HU), 01016

( * ) Notice: Subject to any disclaimer, the term of this patent is extended or adjusted under 35 U.S.C. 154(b) by 0 days.

(21) Appl. No.: 07/985,697

(22) Filed: Dec. 3, 1992

(51) Int. Cl.$^7$ .................. A61K 38/00; A61K 38/04; C07K 16/00; C07K 17/00

(52) U.S. Cl. ........................................ 514/18; 530/330

(58) Field of Search ............................. 514/18; 530/330

(56) References Cited

PUBLICATIONS

Bai et al. Biochem. Pharmacol., 40(8) 1859–1864 (1990).*
Pettit et al. J. Am. Chem. Soc. (1987) 109 6883–6885.*
Pettit et al. J. Med. Chem. (1990) 33, 3132–3133.*

* cited by examiner

*Primary Examiner*—Yvonne Eyler

(57) ABSTRACT

Dolastatin 10, a linear pentapeptide, has shown potent antineoplastic activity profiles against various experimental cancer systems. The synthesis of structural modifications of dolastatin 10 having significant antineoplastic activity against human cancer cell lines has been accomplished; namely antineoplastic tetrapeptide w-amino alkyl amides related to dolastatin 10, which have been found to demonstrate effective antineoplastic activity against various human cancer cell lines. Members of this have demonstrated significant antineoplastic activity against human cancer cell lines. The human cancer cell lines against which the substances of the present invention have yielded the significant antineoplastic activity are: Ovarian OVCAR-3; Central Nervous System ("CNS") SF295; Renal A498; Lung NCI460; Colon KM20L2 and Melanoma SK-MEL-3.

6 Claims, No Drawings

ELUCIDATION AND SYNTHESIS OF ANTINEOPLASTIC TETRAPEPTIDE W-AMINOALKYL-AMIDES

INTRODUCTION

This invention relates generally to the field of antineoplastic compounds, and more particularly to the design and synthesis of selected structural modifications of certain peptides isolated from the Indian Ocean sea hare *Dolabela auriculaia*, namely the tetrapeptide w-amino alkyl amides of dolastatin 10, which have been found to demonstrate effective antineoplastic activity against various human cancer cell lines. Financial assistance for this project was provided by U.S. Government Grant Number OIG-CA44344-O1A1-2: the United States Government may own certain rights to this invention.

BACKGROUND OF THE INVENTION

A great number of ancient marine invertebrate species in the Phyla Bryozoa, Mollusca and Porifera were well established in the earth's oceans over one billion years ago. Certainly such organisms had explored trillions of biosynthetic reactions in their evolutionary chemistry to reach present levels of cellular organization, regulation and defense. Marine sponges have changed minimally in physical appearance for nearly 500 million years, suggesting a very effective chemical evolution in response to changing environmental conditions for at least that time period. Some recognition of the potential for utilizing biologically potent marine animal constituents was recorded in Egypt about 2,700 BC, and by 200 BC sea hare extracts were being used in Greece for medicinal purposes. Such considerations, combined with the general observation that marine organisms (especially invertebrates and sharks) rarely develop cancer, led to the first systematic investigation of marine animal and plant anticancer constituents.

By 1968 ample evidence had been obtained, based on the U.S. National Cancer Institute's key experimental cancer systems, that certain marine organisms would provide new and structurally novel antineoplastic and/or cytotoxic agents. Analogous considerations suggested that marine organisms could also provide effective new drugs for other severe medical challenges, such as viral diseases. Furthermore, marine organisms were expected to contain potentially useful drug candidates (and biochemical probes) of unprecedented structural types, that would have eluded discovery by contemporary techniques of medicinal chemistry. Fortunately these expectations have been realized in the intervening period. Illustrative of these successes are discoveries of the bryostatins, dolastatins, and cephalostatins where five members of these series of remarkable anticancer drug candidates are either now in human clinical trial or preclinical development.

As is well known to those presently engaged in medical research, the time between the isolation of a new compound, and its introduction to the market place takes at least several years in the best case, and can take several decades, when an entity to finance the tortuous regulatory trail is slow to appear.

Consequently, industry, in association with. the government, has devised a number of qualifyng tests which serve two purposes. One aim is to eliminate those ssubstances whose results in the qualifiers unequivocally demonstrate that the further expenditure of funds thereon would be economically counterproductive. The second, and primary aim, is to identify those substances which demonstrate a high likelihood of success and therefore warrant the requisite further investment necessary to obtain the data which is required to meet the various regulatory requirements imposed by those governments which regulate the market place into which such substances will enter.

The present cost of obtaining such data approaches Ten Million Dollars ($10,000,000 U.S.) per compound. Economics dictate that such an investment be made only when there is a reasonable opportunity for it to be recovered. This opportunity can only be provided through patent protection. Absent such protection, there will be no such investment, and the advances in such life saving drugs will stop.

Only two hundred years ago, many diseases ravaged humankind. Many of these diseases have been controlled or eradicated. In the development of the means to treat or control these diseases, work with the appropriate common experimental animals was of critical importance. With the various types of cancers, and with the HIV virus, such work is presently ongoing. The research for the treatment of various types of cancer is coordinated by the National Cancer Institute (NCI). NCI, as a government entity, has been charged with assisting anti-cancer research. To establish whether a substance has anti cancer activity, NCI has established a protocol. This protocol, which involves testing a substance against a cell line panel containing 60 human tumor cell lines, has been verified, and is accepted in scientific circles. This protocol, and the established statistical means of evaluating the results obtained therefrom have been amply described in the literature. See e.g. *Principles & Practice of Oncology* PPO Updates, Volume 3, Number 10, October 1989, by Michael R. Boyd, M. D., Ph.D., for a description of the protocol. The statistical analysis is explained in "Display and Analysis of Patterns of Differential Activity of Drugs Against Human Tumor Cell Lines: Development of Mean Graph and COMPARE Algorithm" *Journal of the National Cancer Institute* Reports Vol. 81, No. 14, Pg. 1088, July 14, 1989, by K. D. Paull et al. Both articles are incorporated herein by this reference as if fully set forth.

The Constitution of the United States (Art. 1, Sec.8), authorizes Congress to establish the United States Patent and Trademark Office(USPTO) to promote scientific advancement. This obligation can only be fully met when the USPTO accepts current medical and scientific realities in the area of medical research.

The Framers of the Constitution meant for the Patent system to advance, not hamstring, scientific advancement. Cells are alive. The impairment of human tumor cell growth is utility. The sole right obtained by the grant of Letters Patent is that of preventing others from exploiting the subject matter of the patent. The recognition of cell line testing as evidence of antineoplastic activity and hence utility can only aid research in the United States, and will prevent the citizens of the United States from being held hostage by foreign governments or foreign corporations, which could otherwise procede with such projects in a less stringent environment, especially if such research is no longer viable in the United States.

Numerous compounds have been discovered which demonstrate significant antineoplastic activity. As discussed above, many of these compounds have been extracted, albeit with great difficulty, from living creatures such as the sponge or the sea hare. However, once the isolation and testing of such compounds has progressed, a practical problem exists, namely, how to obtain a significant quantity of the compound.

Unlike cinchona bark which was collected to produce quinine, and has an excellent yield, the collection and processing of these compounds in their natural occurring state ranges from the grossly impractical to the utterly impossible. Even ignoring potential ecological effects, the population of such creatures is clearly insufficient.

Accordingly, the elucidation of the absolute structure of such an antineoplastic compound is essential. After the absolute structure has been determined, then means of synthesis must be discovered. Additionally, research is essential to the determination of whether any portion of the naturally occurring compound is irrelevant to the desired properties thereof, which aids in determining the simplest structure which needs to be synthesized in order to obtain the perceived antineoplastic properties.

BRIEF DESCRIPTION OF THE INVENTION

Marine organisms, such as various species of sea hares and sponges continue to produce numerous cyclic and linear peptides that contain unprecedented amino acids which exhibit various important biological activities. Such peptides comprise a promising area of inquiry for the discovery of new anticancer drugs. Several of the dolastatins isolated from the Indian Ocean sea hare *Dolabella auriculana* have proved to be remarkably potent antineoplastic substances representing completely new structural types. Presently, dolastatin 10, a linear pentapeptide, has shown the most potent antineoplastic activity profiles, of the dolastatins, against various experimental cancer systems. Substantial research effort has been devoted to an attempt to better understand the reasons for this unusual efficacy. The absolute configuration of dolastatin 10 has recently been discovered. In addition, investigation as to means of synthesis has progressed. Total synthesis has been accomplished. Earlier, dolastatin 10 chiral isomers were prepared. More recently these experiments were extended to the synthesis of R-Doe-isodolastatin 10. This chiral isomer did not show any significant difference in its human cancer cell line activity as compared to dolastatin 10. That, in turn suggested that the 2-thiazolyl unit might not be important and could be replaced with a simple amide.

Accordingly, the elucidation and synthesis of antineoplastic tetrapeptide w-amino alkyl-amides of dolastatin 10 having significant antineoplastic activity against human cell line tumors, is the object of the, subject invention.

This and still further objects as shall hereinafter appear are readily fulfilled by the present invention in a remarkably unexpected manner as will be readily discerned from the following detailed description of an exemplary embodiment thereof.

DESCRIPTION OF THE PREFERRED EMBODIMENT

Marine organisms continue to produce numerous cyclic and linear peptides that contain unprecedented amino acids which exhibit various important biological activities. Such peptides comprise a promising approach to discovery of new anticancer drugs. Several of the dolastatins isolated from the Indian Ocean sea hare *Dolabella auricularia* have proved to be remarkably potent antineoplastic substances representing completely new structural types. Presently dolastatin 10, a linear pentapeptide has shown the most potent antineoplastic activity profiles against various experimental cancer systems. Recently the total synthesis and the absolute configuration of this structurally unique and biologically active peptide was reported. This report has begun to attract increasing interest. Accordingly research on possibly useful isomers of dolastatin 10 continued.

Earlier a series of dolastatin 10 chiral isomers was prepared. More recently these experiments were extended to synthesis of R-Doe-isodolastatin 10. /This chiral isomer did not show any significant difference in its human cancer cell line activity as compared to dolastatin 10. In turn that suggested that the 2-thiazolyl unit may not be too important and might be replaced.

First the importance of the aromatic ring using a 2-pyridyl group was evaluated. Then a saturated heterocyclic ring was investigated using the 4-morpholino group. The corresponding amines (2a–b) were allowed to react with dolaproine (1). Synthesis of amides 3a–b using dimethylphosphorocyanidate (DEPC) for condensation led to excellent yields. No racemization was observed during this reaction.

Next the necessity of having a ring in this unit was investigated by replacing Doe with amides derived from w-dialkylamino-alkylamines. In addition, the importance of the amide molecular length starting with 2-dimethylamino-1-ethylamine (2c) and 3-dimethylamino-1-propylamine (2d) was evaluated.

In each case the synthesis began with a solution of [2S-[2R*(αS*βS*)]]-1-[(1,1-dimethylethoxy)carbonyl]-β-methoxy-ax-methyl-2-pyrrolidinepropanoic acid (t-Boc-Dolaproine, 1, 0.144 g, 0.5 mmol), which was dissolved in 3 ml dichloromethane distilled from $CaH_2$. To this solution was added the respective amine (2a–d 0.5 mmol) followed by triethylamine (0.077 ml, 0.55 mmol) and diethyl phosphorocyanidate (DEPC, 0.09 ml, 93%, 0.55 mmol, ice bath). The solution was stirred under argon for two hours. The solvent was removed (under vacuum at room temperature) and the residue was chromatographed (silica gel column using hexane-acetone 3:1 as eluent). After the evaporation of solvent from the fractions (selected by TLC) 2 ml dry dichloromethane was added and evaporation was repeated. The residue was dried in a desiccator under vacuum overnight to afford the amide (3a–d), which was generally found as a viscous oil, having the structural formula shown in figure 1 below.

A solution of the amide 3a–d (0.2 mmol) in dichloromethane (2 ml) and trifluoroacetic acid (2 ml) was then stirred (ice bath under an argon atmosphere) for two hours. The solvent was removed under reduced pressure and the residue dissolved in toluene. Solvent was again removed in vacuum and this operation was repeated. The residue was dried in a desiccator (under vacuum overnight) to afford the trifluoroacetate salt 4a–d generally found as a viscous oil.

To a solution of the trifluoroacetate salt 4a–d (0.2 mmol) in dichloromethane (2 ml, distilled from $CaH_2$) was added the tripeptide trifluoroacetate salt (5, 0.109 g, 0.2 mmol) followed by triethylamine (0.088 ml, 0.63 mmol) and diethyl phosphorocyanidate (DEPC, 0.036 ml, 93%, 0.22 mmol, ice bath). The solution was stirred under argon for two hours. The solvent was removed (under vacuum at room temperature) and the residue was chromatographed (silica gel column using acetone-hexane 3:2 as eluent). After the evaporation of solvent from the fractions (selected by TLC behaviour) 2 ml of dry dichloromethane was added evaporated. The residue was dried in a desiccator under vacuum overnight to yield a white fluffy solid, yielding the tetrapeptide w-aminoalkylamides 6a–d.

The extraordinary inhibition of cell growth shown by the tetrapeptide w-aminoalkylamides 6a–d against six major types of human cancer and against the murine P388 lymphocytic leukemia cell line has been presented in Table I.

added and evaporation was repeated. The residue was dried in a dessicator under vacuum overnight to afford the amide 3a–d as a viscous oil.

EXAMPLE Ia

Synthesis of Compound 3a
[2S-[2R*[1S*,2S*]]]-2-[1-methoxy-2-methyl-3-oxo-3-[[2-(2-pyridyl)ethyl]amino]propyl]-1-pyrrolidinecarboxyllc acid, 1,1-dimethylethylester (3a)

Compound 3a was synthesized from t-Boc-Dolaproine (1) and 2-(2-aminoethyl)pyridine (2a) according to General

TABLE 1

The Powerful Cancer Cell Growth Inhibitory Activity of Peptides 6a–d

|  | Cell type | Cell line | 6a | 6b | 6c | 6d |
|---|---|---|---|---|---|---|
| Mouse leukemia cell |  | P-388 | 0.000713 | 0.0736 | <0.1 | 0.881 |
| Human cancer cell | Ovarian | OVCAR-3 | 0.000039 | <0.0001 | 0.0028 | <0.01 |
| GI-50 ($\mu$g/ml) | CNS | SF-295 | 0.000350 | <0.0001 | 0.0033 | <0.01 |
|  | Renal | A498 | 0.000430 | <0.0001 | 0.0025 | <0.01 |
|  | Lung-NSC | NCI-460 | 0.000240 | <0.0001 | 0.0051 | 0.0072 |
|  | Colon | KM20L2 | 0.000062 | <0.0001 | <0.01 | <0.01 |
|  | Melanoma | SK-MEL-3 | 0.000065 | <0.0001 | <0.01 | <0.01 |
| Human cancer cell | Ovarian | OVCAR-3 | 0.00021 | <0.0001 | 0.0086 | <0.01 |
| TGI ($\mu$g/ml) | CNS | SF-295 | <0.01 | <0.0001 | <0.01 | <0.01 |
|  | Renal | A498 | <0.01 | <0.0001 | 0.0056 | <0.01 |
|  | Lung-NSC | NCI-460 | 0.00080 | <0.0001 | <0.01 | <0.01 |
|  | Colon | KM20L2 | 0.00110 | <0.0001 | <0.01 | <0.01 |
|  | Melanoma | SK-MEL-3 | 0.00077 | <0.0001 | <0.01 | <0.01 |
| Human cancer cell | Ovarian | OVCAR-3 | <0.01 | <0.0001 | <0.01 | <0.01 |
| LC-50 ($\mu$g/ml) | CNS | SF-295 | <0.01 | <0.0001 | <0.01 | <0.01 |
|  | Renal | A498 | <0.01 | <0.0001 | <0.01 | <0.01 |
|  | Lung-NSC | NCI-460 | <0.01 | <0.0001 | <0.01 | <0.01 |
|  | Colon | KM20L2 | <0.01 | <0.0001 | <0.01 | <0.01 |
|  | Melanoma | SK-MEL-3 | <0.01 | <0.0001 | <0.01 | <0.01 |

To further aid in the understanding of the present invention and not by way of limitation, the following examples are presented.

EXAMPLE I

Synthesis of Amides 3a–d
General Procedure A.

To a solution of [2S-[2R*(aS*,bS*)]]-1-[(1,1-dimethylethoxy)carbonyl]-b-methoxy-a-methyl-2-pyrrolidinepropanoic acid (t-Boc-Dolaproine, 1, 0.0861 g, 0.3 mmol) in dichloromethane (2 ml, distilled from CaH$_2$) was added the respective amine (2a–d 0.5 mmol) followed by triethylamine (0.046 ml, 0.33 mmol) and diethyl phosphorocyanidate (DEPC, 0.054 ml, 93%, 0.33 mmol, ice bath) and the solution was stirred under vacuum for two hours. The solvent was removed (under vacuum at room temperature) and the residue was chromatographed (silica gel column). After the evaporation of solvent from the fractions (selected by TLC) 2 ml dry dichloromethane was Procedure A. The crude reaction mixture was purified via column chromatograhy by use of silica gel with hexane-acetone 1:1 as eluent.

Yield 3a: 0.109 g (93%) [a]$^P_{25}$:–35.(0.62, c, CHCl$_3$) Anal. Calc.: C$_{21}$H$_{33}$N$_3$O$_4$ Mw.: 391.49

EXAMPLE Ib

Synthesis of Compound 3b
[2S-[2R*[1S*,2S*]]]-2-[1-methoxy-2-methyl-3-oxo-3-[[2-(4-morpholino)ethyl]amino]propyl]-1-pyrrolidinecarboxylic acid, 1,1-dimethylethylester (3b)

Compound 3b was synthesized from t-Boc-Dolaproine (1) and 4-(2-aminoethyl)-morpholine (2b) according to General Procedure A. The crude reaction mixture was purified via column chromatograhy by use of silica gel with acetone-hexane 2:1 as eluent.

Yield 3b: 0.091 g (76%) [a]$_D^{25}$=–37.9 (c 1.63, CHCl$_3$) Anal. Calcd for C$_{20}$H$_{37}$N$_3$O$_5$, M. w.: 399.52

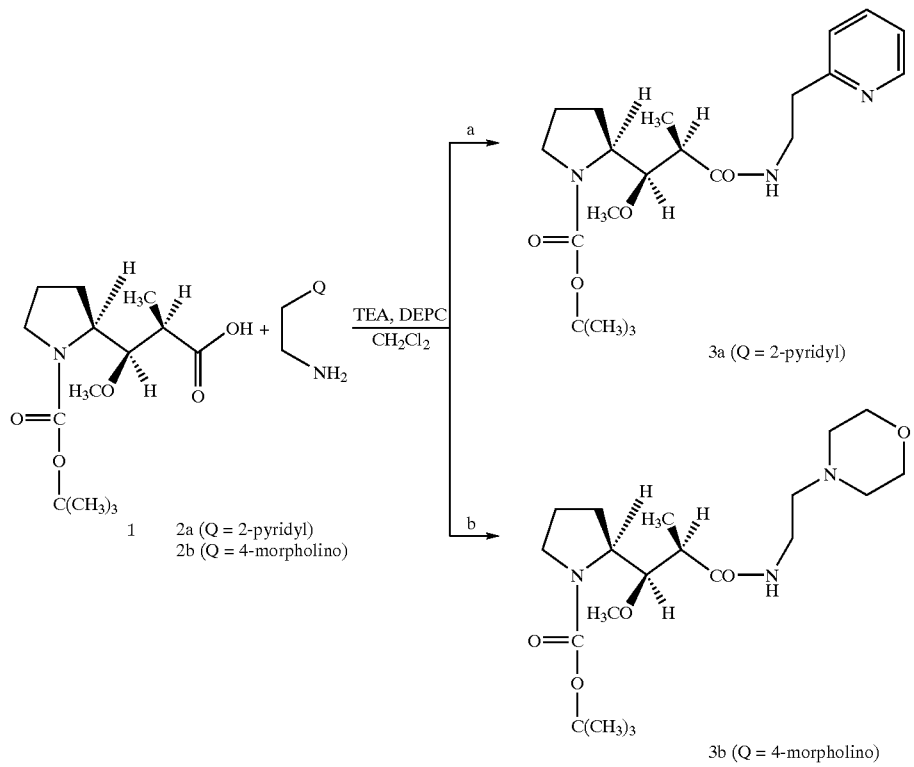

EXAMPLE Ic

Synthesis of Compound 3c

[2S-[2R*[1S*,2S*]]]-2-[1-methoxy-2-methyl-3-oxo-3-[[2-dimethylamino-ethyl]amino]propyl]-1-pyrrolidinecarboxylic acid, 1,1-dimethylethylester (3c)

Compound 3c was synthesized from t-Boc-Dolaproine (1) and 2-dimethylamino-1-ethylamine (2c) according to General Procedure A. The crude reaction mixture was purified via column chromatograhy by use of silica gel with acetone-methanol 1:1 as eluent.

Yield 3c: 0.073 g (68%) $[a]^P_{25}$:−57.1 (0.31, c, CHCl$_3$)
Anal. Calc. : $C_{18}H_{35}N_3O_4$ Mw.: 357.481

EXAMPLE Id

Synthesis of Compound 3d

[2S-[2R*[1S*,2S*]]]-2-[1-methoxy-2-methyl-3-oxo-3-[[3-dimethylamino-propyl]amino]propyl]-1-pyrrolidinecarboxylic acid, 1,1-dimethylethylester (3d)

Compound 3d was synthesized from t-Boc-Dolaproine (1) and 3-dimethylamino-1-propylamine (2d) according to General Procedure A. The crude reaction mixture was purified via column chromatograhy by use of silica gel with acetone-methanol 1:1 as eluent.

Yield 3d: 0.074 g (66%) $[a]_D^{25}$=−42.7 (c=0.34 in CHCl$_3$)
Anal. Calcd for $C_{19}H_{37}N_3O_4$ M. w.: 371.51

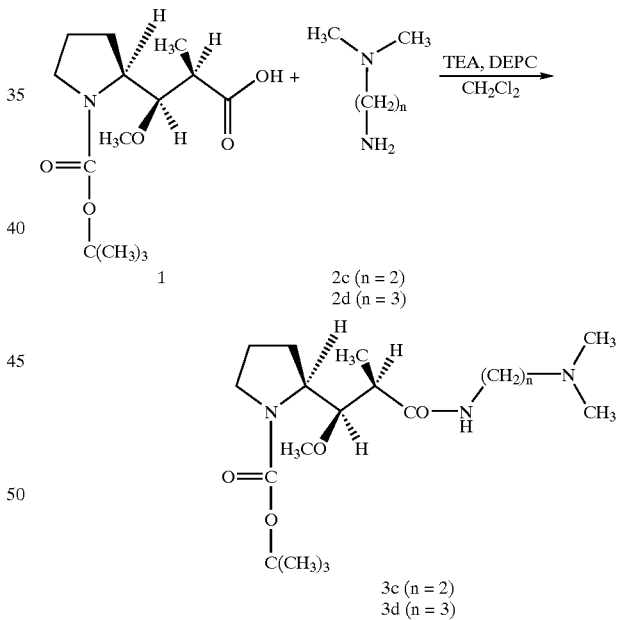

EXAMPLE II

The protecting groups of amides 3a–d from Example I was removed with trifluoroacetic acid to afford the trifluoroacetate salts 4a–d, in the following manner, as shown below. A solution of the amide 3a–d (0.2 mmol) in dichloromethane (2 ml) and trifluoroacetic acid (2 ml) was stirred (ice bath under an argon atmosphere) for two hours. The solvent was removed under reduced pressure and the residue dissolved in toluene. Solvent was again removed in vacuum and this operation was repeated. The residue was dried in a dessicator (under vacuum overnight) to afford the trifluoroacetate salt 4a–d as a viscous oil.

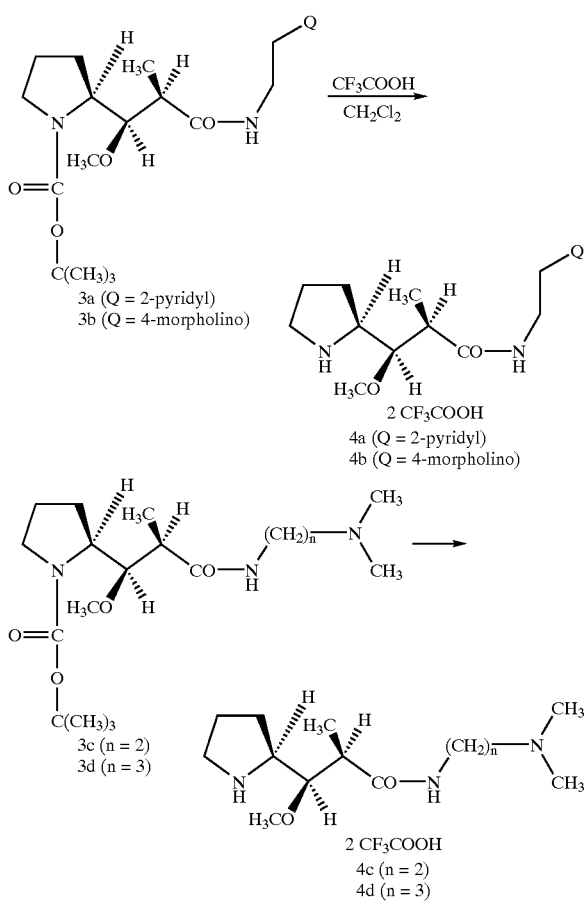

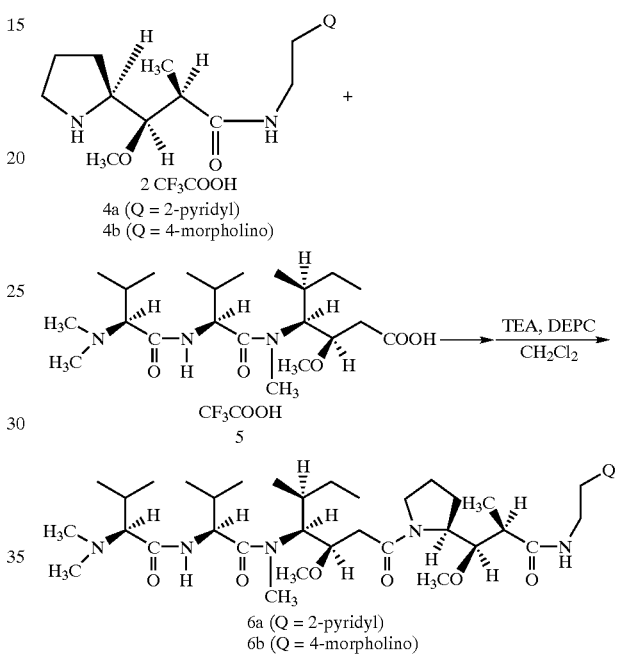

EXAMPLE III

Synthesis of Peptides 6a–d

General Procedure B.

To a solution of the trifluoroacetate salt 4a–d (0.2 mmol) in dichloromethane (2 ml, distilled from $CaH_2$) was added the tripeptide (synthesis previously reported) trifluoroacetate salt (5, 0.109 g, 0.2 mmol) followed by triethylamine (0.115 ml, 0.83 mmol) and diethyl phosphorocyanidate (DEPC, 0.036 ml, 93%, 0.22 mmol, ice bath). The solution was stirred under vacuum for two hours. The solvent was removed (under vacuum at room temperature) and the residue was chromatographed (silica gel column). After the evaporation of solvent from the fractions (selected by TLC behaviour) 2 ml of dry dichloromethane was added and evaporated. The residue was dried in a dessicator under vacuum overnight to yield a white fluffy solid.

EXAMPLE III a

Synthesis of Peptide 6a
[2S-[1[1R*(R*),2S*],2R*[1S*,2S*]]]-N,N-dimethyl-L-valyl-N-[2-methoxy-4-[2-[1-methoxy-2-methyl-3-oxo-3-[[2-(2-pyridyl)ethyl]amino]propyl]-1-pyrrolidinyl-1-(methylpropyl)-4-oxobutyl]-N-methyl-L-valineamide (6a)

Compound 6a was synthesized from trifluoroacetate salt 4a (from amide 3a) and tripeptide trifluoroacetate salt 5 by General Procedure B. The crude reaction mixture was purified via column chromatograhy by use of silica gel with tetrahydrofuran-hexane-acetone 7:2:3 as eluent.

Yield 6a: 0.125 g (89%) M. p.: 65–68° C. $[a]^P_{25}$:-37.5 (c=0.12 in $CHCl_3$) Anal. Calc.: $C_{39}H_{66}N_6O_6$ Mw.: 702.955

EXAMPLE III b

Synthesis of Peptide 6b
[2S-[1[1R*(R*),2S*],2R*[1S*,2S*]]]-N,N-dimethyl-L-valyl-N-[2-methoxy-4-[2-[1-methoxy-2-methyl-3-oxo-3-[[2-(4-morpholino)ethyl]amino]propyl]-1-pyrrolidinyl-1-(methylpropyl)-4-oxobutyl]-N-methyl-L-valineamide (6b)

Compound 6b was synthesized from trifluoroacetate salt 4b (from amide 3b) and tripeptide trifluoroacetate salt 5 by General Procedure B. The crude reaction mixture was purified via column chromatograhy by use of silica gel with methanol-ethyl acetate 1:1 as eluent.

Yield 6b : 0.112 g (79%) M. p.: 148–151° C. $[a]_D^{25}$=−31.5 (c=0.55 in $CH_3OH$) Anal. Calc.: $C_{37}H_{70}N_6O_7$ Mw.: 710.98

EXAMPLE III c

Synthesis of Peptide 6c
[2S-[1[1R*(R*),2S*],2R*[1S*,2S*]]]-N,N-dimethyl-L-valyl-N-[2-methoxy-4-[2-[1-methoxy-2-methyl-3-oxo-3-[[2-dimethylamino-ethyl]amino]propyl]-1-pyrrolidinyl-1-(methylpropyl)-4-oxobutyl]-N-methyl-L-valineamide (6c)

Compound 6c was synthesized from trifluoroacetate salt 4c (from amide 3c) and tripeptide trifluoroacetate salt 5 by General Procedure B. The crude reaction mixture was purified via column chromatograhy by use of silica gel with methanoltetrahydrofuran 8:2 as eluent.

Yield 6c: 0.094 g (70%) M. p.: 78–80° C. $[a]^P_{25}$:-51.3 (c=0.16 in $CHCl_3$) Anal. Calc.: $C_{35}H_{68}N_6O_6$ Mw.: 668.944

EXAMPLE III d

Synthesis of Peptide 6d
[2S-[1[1R*(R*),2S*],2R*[1S*,2S*]]]-N,N-dimethyl-L-valyl-N-[2-methoxy-4-[2-[1-methoxy-2-methyl-3-oxo-3-[[3-dimethylamino-propyl]amino]propyl]-1-pyrrolidinyl-1-(methylpropyl)-4-oxobutyl]-N-methyl-L-valineamide (6d)

Compound 6d was synthesized from trifluoroacetate salt 4d (from amide 3d) and tripeptide trifluoroacetate salt 5 by General Procedure B. The crude reaction mixture was purified via column chromatograhy by use of silica gel with methanoltetrahydrofuran 9:1 as eluent.

Yield 6d: 0.094 g (69%) M. p.: 62–66° C. $[a]_D^{25}$=−62.1 (c=0.43 in $CHCl_3$) Anal. Calc.: $C_{36}H_{70}N_6O_6$ Mw.: 682.97

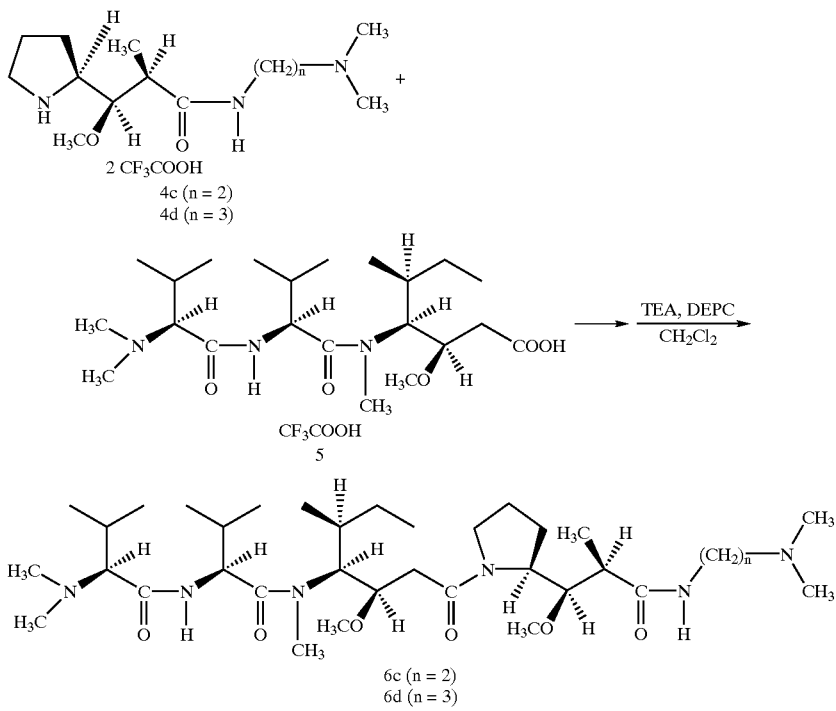

4c (n = 2)
4d (n = 3)

5

6c (n = 2)
6d (n = 3)

From the foregoing, it is readily apparent that new and useful embodiments of the present invention have been herein described and illustrated which fulfill all of the aforestated objectives in a remarkably unexpected fashion. It is of course understood that such modifications, alterations and adaptations as may readily occur to the artisan confronted with this disclosure are intended within the spirit of this disclosure which is limited only by the scope of the claims appended hereto.

---

Accordingly, we claim the following:

1. A composition of matter having the general structure:

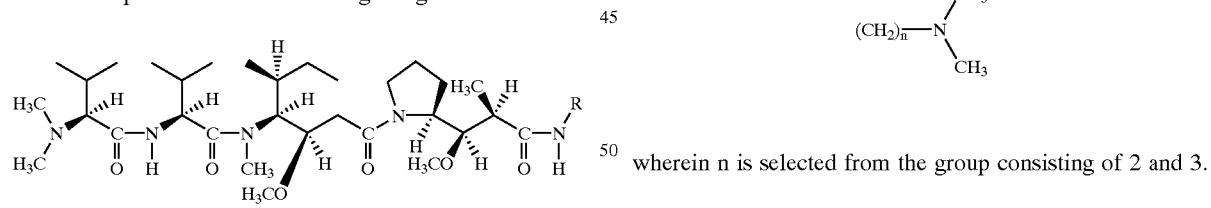

wherein R is selected from the group consisting of 2-pyridyl, 4-morpholino and wherein n is selected from the group consisting of 2 and 3.

2. A composition of matter according to claim 1 having the structural formula shown below wherein n is selected from the group consisting of 2 and 3:

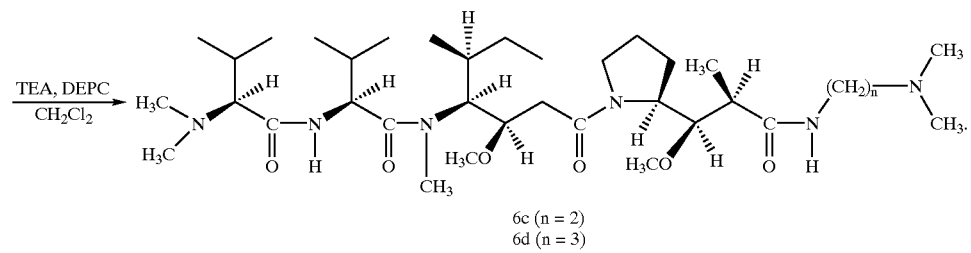

6c (n = 2)
6d (n = 3)

3. A composition of matter according to claim 1 having the following structure wherein Q is selected from the group consisting of 2-pyridyl and 4-morpholino:

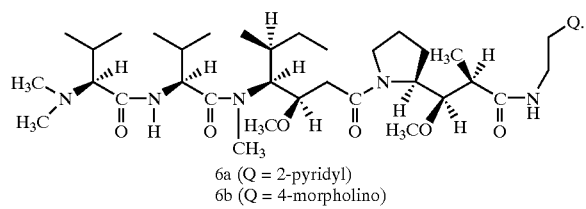

6a (Q = 2-pyridyl)
6b (Q = 4-morpholino)

4. A pharmaceutical preparation comprising as its essential active ingredient a compound having the structure set forth in claim 1.

5. A pharmaceutical prepartion according to claim 2, wherein n is selected from the group consisting of 2, and 3.

6. A pharmaceutical preparation according to claim 3 wherein Q is selected from the the group consisting of 2-pyridyl and 4-morpholino.

* * * * *

UNITED STATES PATENT AND TRADEMARK OFFICE
CERTIFICATE OF CORRECTION

PATENT NO. : 6,569,834 B1
DATED : May 27, 2003
INVENTOR(S) : Pettit et al.

It is certified that error appears in the above-identified patent and that said Letters Patent is hereby corrected as shown below:

Column 1,
Line 11, change italicized "Dolabela" to italicized -- Dolabella --.
Line 12, change italicized "auriculaia" to italicized -- auricularia --.

Column 3,
Line 31, change italicized "auriculana" to italicized -- auricularia --.

Column 4,
Line 14, change "/This" to -- This --.
Line 23, change "dimethylphosphorocyanidate" to -- diethylphosphorocyanidate --.

Line 37, change "methodxy-ax-methyl" to 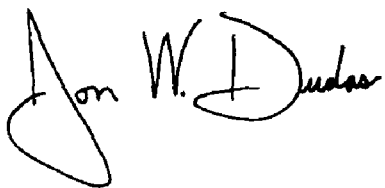 -- methodxy-α-methyl --.

Column 6,
Line 9, change "1-pyrrolidinecarboxyllc" to -- 1-pyrrolidinecarboxylic --.

Columns 15 and 16,
Delete the following portion from the formula appearing in claim 2:

" $\xrightarrow[CH_2Cl_2]{TEA, DEPC}$ ".

Signed and Sealed this

Thirteenth Day of April, 2004

JON W. DUDAS
*Acting Director of the United States Patent and Trademark Office*

SEQUENCE LISTING (1) GENERAL INFORMATION:

(iii) NUMBER OF SEQUENCES: 4

(2) INFORMATION FOR SEQ ID NO: 1:

(i) SEQUENCE CHARACTERISTICS:
    (A) LENGTH: 4 amino acid residues
    (B) TYPE: amino acid
    (D) TOPOLOGY: linear (ii) MOLECULE TYPE:
    (A) DESCRIPTION: Linear tetrapeptideamide (iii) HYPOTHETICAL: no (iv) ANTI-SENSE: no (v) FRAGMENT TYPE: C terminal (ix) FEATURE:
    (A) NAME/KEY: [2S-[1[1R*(R*),2S*],2R*[1S*,2S*]]]-
       N,N-dimethyl-L-valyl-N-[2-methoxy-4-[2-[1-methoxy-2-
       methyl-3-oxo-3-[[2-(2-pyridyl)ethyl]amino]propyl]-1-
       pyrrolidinyl-1-(methylpropyl)-4-oxobutyl]-N-methyl-L-
       valineamide (B) IDENTIFICATION METHOD: by experiment using high resolution
    nuclear magnetic resonance and mass spectral techniques
(C) OTHER INFORMATION: this tetrapeptideamide is
    cell growth inhibitory peptide derivative (xi) SEQUENCE DESCRIPTION: SEQ ID NO: 1:

Xaa Val Xaa Xaa (2) INFORMATION FOR SEQ ID NO: 2:

(i) SEQUENCE CHARACTERISTICS:
       (A) LENGTH: 4 amino acid residues
       (B) TYPE: amino acid
       (D) TOPOLOGY: linear (ii) MOLECULE TYPE:
       (A) DESCRIPTION: Linear tetrapeptideamide (iii) HYPOTHETICAL: no (iv) ANTI-SENSE: no (v) FRAGMENT TYPE: C terminal (ix) FEATURE:
       (A) NAME/KEY: [2S-[1[1R*(R*),2S*],2R*[1S*,2S*]]]-
           N,N-dimethyl-L-valyl-N-[2-methoxy-4-[2-[1-methoxy-2-
           methyl-3-oxo-3-[[2-(4-morpholino) ethyl)amino]
           propyl]-1-pyrrolidinyl-1-(methylpropyl)-4-oxobutyl]-
           N-methyl-L-valineamide
       (B) IDENTIFICATION METHOD: by experiment using
           high resolution nuclear magnetic resonance and mass
           spectral techniques
       (C) OTHER INFORMATION: this tetrapeptideamide is
           cell growth inhibitory peptide derivative (xi) SEQUENCE DESCRIPTION: SEQ ID NO: 2:

Xaa Val Xaa Xaa (2) INFORMATION FOR SEQ ID NO: 3:

(i) SEQUENCE CHARACTERISTICS:
       (A) LENGTH: 4 amino acid residues
       (B) TYPE: amino acid
       (D) TOPOLOGY: linear (ii) MOLECULE TYPE:
       (A) DESCRIPTION: Linear tetrapeptideamide (iii) HYPOTHETICAL: no (iv) ANTI-SENSE: no (v) FRAGMENT TYPE: C terminal (ix) FEATURE:
       (A) NAME/KEY: [2S-[1[1R*(R*),2S*],2R*[1S*,2S*]]]-
           N,N-dimethyl-L-valyl-N-[2-methoxy-4-[2-[1-methoxy-2-
           methyl-3-oxo-3-[[2-dimethylaminoethyl]amino]propyl]-
           1-pyrrolidinyl-1-(methylpropyl)-4-oxobutyl]-N-
           methyl-L-valineamide
       (B) IDENTIFICATION METHOD: by experiment using
           high resolution nuclear magnetic resonance and mass
           spectral techniques
       (C) OTHER INFORMATION: this tetrapeptideamide is
           cell growth inhibitory peptide derivative (xi) SEQUENCE DESCRIPTION: SEQ ID NO: 3:

Xaa Val Xaa Xaa (2) INFORMATION FOR SEQ ID NO: 4:

(i) SEQUENCE CHARACTERISTICS:
        (A) LENGTH: 4 amino acid residues
        (B) TYPE: amino acid
        (D) TOPOLOGY: linear (ii) MOLECULE TYPE:
        (A) DESCRIPTION:  Linear tetrapeptideamide (iii) HYPOTHETICAL: no (iv) ANTI-SENSE:    no (v) FRAGMENT TYPE: C terminal (ix) FEATURE:
        (A) NAME/KEY: [2S-[1[1R*(R*),2S*],2R*[1S*,2S*]]]-
            N,N-dimethyl-L-valyl-N-[2-methoxy-4-[2-[1-methoxy-2-
            methyl-3-oxo-3-[[3-dimethylaminopropyl]
            amino]propyl]-1-pyrrolidinyl-1-(methylpropyl)-4-
            oxobutyl]-N-methyl-L-valineamide
        (B) IDENTIFICATION METHOD:  by experiment using
            high resolution nuclear magnetic resonance and mass
            spectral techniques
        (C) OTHER INFORMATION: this tetrapeptideamide is
            cell growth inhibitory peptide derivative (xi) SEQUENCE DESCRIPTION: SEQ ID NO: 4:

Xaa Val Xaa Xaa